(12) United States Patent
Iwaszczuk et al.

(10) Patent No.: US 9,983,125 B2
(45) Date of Patent: May 29, 2018

(54) DETECTION OF TERAHERTZ RADIATION

(71) Applicant: Danmarks Tekniske Universitet, Kgs. Lyngby (DK)

(72) Inventors: Krzysztof Iwaszczuk, Copenhagen N (DK); Peter Uhd Jepsen, Copenhagen S (DK)

(73) Assignee: Danmarks Tekniske Universitet, Kgs. Lyngby (DK)

( * ) Notice: Subject to any disclaimer, the term of this patent is extended or adjusted under 35 U.S.C. 154(b) by 0 days. days.

(21) Appl. No.: 14/915,473

(22) PCT Filed: Aug. 29, 2014

(86) PCT No.: PCT/DK2014/050259
§ 371 (c)(1),
(2) Date: Feb. 29, 2016

(87) PCT Pub. No.: WO2015/028029
PCT Pub. Date: Mar. 5, 2015

(65) Prior Publication Data
US 2016/0216201 A1    Jul. 28, 2016

(30) Foreign Application Priority Data
Aug. 29, 2013   (EP) ..................... 13182239

(51) Int. Cl.
*G01J 3/28*    (2006.01)
*G01N 21/35*   (2014.01)
*H01L 31/0232* (2014.01)
*G01N 21/3581* (2014.01)

(52) U.S. Cl.
CPC ............ *G01N 21/3581* (2013.01); *G01J 3/28* (2013.01); *H01L 31/0232* (2013.01); *G01N 2201/0633* (2013.01)

(58) Field of Classification Search
CPC .................. G01J 3/28; G01N 21/3581; G01N 2201/0633; H01L 31/0232
See application file for complete search history.

(56) References Cited

U.S. PATENT DOCUMENTS

| | | | |
|---|---|---|---|
| 2001/0029436 A1 | 10/2001 | Fukasawa | |
| 2002/0067480 A1* | 6/2002 | Takahashi | G01N 21/3581 356/317 |
| 2012/0241615 A1 | 9/2012 | Tomioka | |
| 2013/0153765 A1 | 6/2013 | Tomioka | |
| 2014/0048710 A1* | 2/2014 | Xu | H01Q 15/0053 250/341.1 |

OTHER PUBLICATIONS

Hirori, H. et al., "Extraordinary carrier multiplication gated by a picosecond electric field pulse" Nature Communications, 2011, pp. 1-6, vol. 2, No. 594.

(Continued)

*Primary Examiner* — Mark R Gaworecki
(74) *Attorney, Agent, or Firm* — Knobbe Martens Olson & Bear LLP

(57) ABSTRACT

The present invention relates to a system for detecting terahertz radiation, a camera device, and a method for detecting terahertz radiation.

11 Claims, 5 Drawing Sheets

(56) References Cited

OTHER PUBLICATIONS

Hsieh, Bing-Yu et al, "Analysis of periodic metallic nano-slits for efficient interaction of terahertz and optical waves at nano-scale dimensions" Journal of Applied Physics, 2011, pp. 084326-1-084326-5, vol. 109.
Tomita, Sakura et al., "Sensing Method Based on the Reflective Property of a Thin Metallic Mesh Device in the Terahertz Region" 2011 Annual Report / Conference on Electrical Insulation and Dielectric Phenomena, Oct. 16, 2011, pp. 292-295.
International Search Report for PCT/DK2014/050259 dated Nov. 11, 2014.

\* cited by examiner

DETECTION OF TERAHERTZ RADIATION

CROSS REFERENCE TO RELATED APPLICATIONS

This application is a U.S. National Phase Application of PCT International Application Number PCT/DK2014/050259, filed on Aug. 29, 2014, designating the United States of America and published in the English language, which is an International Application of and claims the benefit of priority to European Patent Application No. 13182239.7, filed on Aug. 29, 2013. The disclosures of the above-referenced applications are hereby expressly incorporated by reference in their entireties.

FIELD OF THE INVENTION

The present invention relates to a method and device for detection of terahertz radiation.

BACKGROUND OF THE INVENTION

In recent years, increasing attention has been directed to terahertz (THz) waves, which are electromagnetic waves with frequencies of around 100 GHz up to around 30 THz. Terahertz waves can be used in various forms of measurement and non-destructive testing such as imaging and spectroscopy.

Terahertz waves can be generated by many various methods, for example: thermal emitters, molecular lasers, free electron lasers, backward wave oscillators, Schottky diodes, photoconductive switches driven by sub-picosecond optical pulses and nonlinear optical sources based on wave-mixing in nonlinear crystals.

As a detector for detecting terahertz waves an item for converting terahertz waves to heat can be used, specifically, an item that converts terahertz waves to heat, and detects the energy, i.e. intensity, of the terahertz waves. These kinds of detection units include pyroelectric sensors, bolomoters, Golay cells and the like. Such a system is e.g. described in US 2013/0153765. Other commonly used detection schemes include: Schottky diodes, high electron mobility transistors, photoconductive switches driven by sub-picosecond optical pulses and electro-optic sampling.

As heat may be subject to external thermal noise influencing the measurement, an improved method and system would be advantageous, and in particular a more efficient and/or reliable system and/or method for detection of terahertz radiation would be advantageous.

OBJECT OF THE INVENTION

It is an object of the present invention to provide an alternative to the prior art.

In particular, it may be seen as an object of the present invention to provide a detector that solves the above mentioned problems of the prior art.

SUMMARY OF THE INVENTION

The inventors have surprisingly realized that a strong THz pulse can generate ultrafast field emission of electrons from a surface of a metallic layer via nonperturbative nonlinear interactions. The electrons may be accelerated to multi-10-eV kinetic energies by the same enhanced THz field near the metal, and can be used to initiate collision-induced physical processes on an ultrafast time scale, such as formation of a nitrogen plasma. The inventors have further realized that this mechanism may form the basis for compact THz detectors that measure the intensity of THz-induced emission at optical wavelengths, e.g. in the ultra violet (UV), visible (VIS), or near-infrared (NIR) spectrum. Such a detector, unlike those currently known in the art, will be sensitive to the peak THz field in an ungated manner and thus offer new detection capabilities akin to nonlinear optical detectors in the visible and near-infrared. By designing the metallic layer to the desired properties, such as resonance frequency, and bandwidth, the optical signal may be optimized for the application, as will be exemplified below.

Thus, the above-described object and several other objects are intended to be obtained in a first aspect of the invention by providing a system for detecting terahertz radiation. The system comprises an input configured for receiving the terahertz radiation, a metallic layer arranged for receiving the terahertz radiation from the input. Further, the metallic layer comprises an arrangement of metallic structures or apertures in a metallic film. The metallic layer is arranged so as to receive the terahertz radiation, and the metallic layer emits an optical signal in response to the terahertz radiation. The system further comprises an optical sensor arranged to detect the emitted optical signal and to provide a signal indicating a property of the terahertz radiation. The metallic layer is preferably structured so that at least one opening exist. In an alternative embodiment light is emitted to the same side of the metallic layer as the incident terahertz wave.

With such a system it is possible to directly measure the intensity of ultraviolet, visible and near-infrared (UV-VIS-NIR) light generated in or near the structured, metallic layer exposed to the terahertz wave. Detection of the UV-VIS-NIR light may be performed in a very simple manner, using either single pixel devices, such as in photomultiplier tubes, phototubes, photodiodes, avalanche photodiodes, electron multipliers or the like, further the system may be incorporated in multi-pixel devices, such as CCD and CMOS image sensors, microchannel plates and the like.

Unlike methods based on thermal effects, the present method does not measure average terahertz power. Instead, the generated light is related to the peak electric field of the incoming terahertz radiation.

By engineering the resonant properties of the structured metallic layer or layers in the terahertz range, narrowband and broadband detection of terahertz radiation is possible. Also, by engineering the field enhancement properties of the structured metallic layer the sensitivity range of the terahertz detector may be changed.

In an embodiment of the invention, the resonant properties of the structured metallic layer is achieved by structuring the metallic layer so as to form an array of micro-antennas, which antennas are configured to have a resonance frequency falling within a frequency range of the incident terahertz radiation. The inventors have experimentally verified that optical radiation is emitted from regions near the antenna tips, where electromagnetic field enhancement of the antennas are highest.

In one embodiment, the micro-antennas have a symmetric I-shape. In this way, symmetric emission from the two ends of an antenna is achieved.

In another embodiment, the micro-antennas have a T-shape.

In an example according to this embodiment, the crossbar of the "T" is selected to approximately half the length of the vertical bar.

In an alternative embodiment of the invention, the resonant properties of the structured metallic layer is achieved by a random deposition of metal on a carrying surface, so as to form nano- to micrometer-scale islands separated by apertures.

A second aspect of the present invention relates to a camera device comprising a receiver receiving an incident terahertz beam, a detector having a metallic layer arranged for receiving the terahertz beam from the receiver and wherein the metallic layer comprises an arrangement of metallic structures or apertures in a metallic film, the metallic layer emitting an optical signal in response to the terahertz radiation, and an optical sensor arranged to detect the emitted optical signal and to provide a signal indicating a property of the terahertz radiation.

The camera device may then be used to detect terahertz radiation, in 2D or even 3D if needed. The camera may record still images and/or sequences for use as video/moving pictures with or without audio.

A third aspect of the present invention relates to a method for detecting terahertz radiation. The method may comprise a step of providing terahertz radiation at an input. The input may be part of a detector system or as mentioned above, a camera. The method may comprise a step of directing the terahertz radiation at a metallic layer from the input. As mentioned elsewhere the metallic layer may comprise an arrangement of metallic structures or apertures in the metallic film and the metallic layer or the surrounding atmosphere emits an optical signal in response to the terahertz radiation. The method may comprise a step of detecting the emitted optical signal at an optical sensor to provide a signal indicating a property of the terahertz radiation. The detected signal may then be transformed into an electrical signal to be used in a signal processor or the like for processing and determining properties of the terahertz signal.

A fourth aspect relates to the use of a terahertz radiation detector as a gas composition sensor, where the gas detection method is based on spectral analysis of ultraviolet, visible and near-infrared (UV-VIS-NIR) light generated after irradiation of the terahertz radiation detector with the terahertz wave. The presence of the gas surrounding the metallic structures can alter the spectrum of the generated UV-VIS-NIR light. The response from the sensor then undergoes spectral analysis which enables the identification of compounds in the gas. Advantageously identification of compounds in the gas may be performed with the use of algorithms from other spectroscopy methods, and may include comparison with libraries of spectra of known compounds.

The individual aspects of the present invention may each be combined with any of the other aspects. These and other aspects of the invention will be apparent from the following description with reference to the described embodiments.

BRIEF DESCRIPTION OF THE FIGURES

The methods and systems according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

The THz frequency range lays on the borderline of the electronic world, where radio and microwave radiation is easily generated using electron based devices, and the photonic world, where optical techniques are successfully applicable.

THz waves have low photon energies, 4.14 meV for 1 THz, which is approximately a million times weaker than characteristic photon energies of X-rays, and do not cause harmful photoionization or other damage due to linear interactions in biological tissues. For that reason THz radiation is considered completely safe for potential sensing and imaging techniques. THz waves can penetrate, and pass through, many optically opaque nonpolar dielectrics, such as paper, textile, plastic or ceramics with low attenuation.

The THz frequency range hosts low frequency crystalline lattice vibrations—phonon modes, hydrogen-bonding stretches and other intermolecular vibrations and rotational transitions of molecules in many chemical and biological materials, including many explosives and drugs. The wealth of unique spectroscopic signatures in the THz energy range for all states of matter, such as gasses, liquids, solid-state and even plasma, makes the THz spectral range ideal for spectroscopic purposes. Because of its spectroscopic properties combined with the ability to image material under covers or in containers and its non-ionizing photon energies, THz waves are considered highly competitive for nondestructive and noninvasive sensing.

There are several ways to detect terahertz radiation. Historically the oldest detection methods are based on thermal effects. Terahertz light is absorbed in the material and lead to an increase of temperature, which can then be sensed by devices such as bolometers, Golay cells and pyro-detectors. In such devices the temperature change is proportional to the absorbed energy, and thus directly related to the intensity of the terahertz wave.

Because these devices and methods are dependent on heating processes, response times of the devices are slow. Furthermore, the sensitivity is low and often requires cryogenic cooling in order to suppress thermal noise.

A newer class of detectors comes from an electronic approach and include Schottky diode mixers, high electron mobility transistors and many others. At least one limitation of the electronic approach is a low upper limit on bandwidth the devices, typically few hundred GHz.

Other ways of detecting terahertz transients is by using photoconductive switches, electro-optic sampling and air-biased coherent detection. Magneto-optic sampling, terahertz enhanced fluorescence and terahertz enhanced acoustics can also be used. These methods allow mapping of the temporal profile of the terahertz electromagnetic wave, but all require at least one optical probe beam, which is synchronized and phase locked to the terahertz wave.

Figure 1:
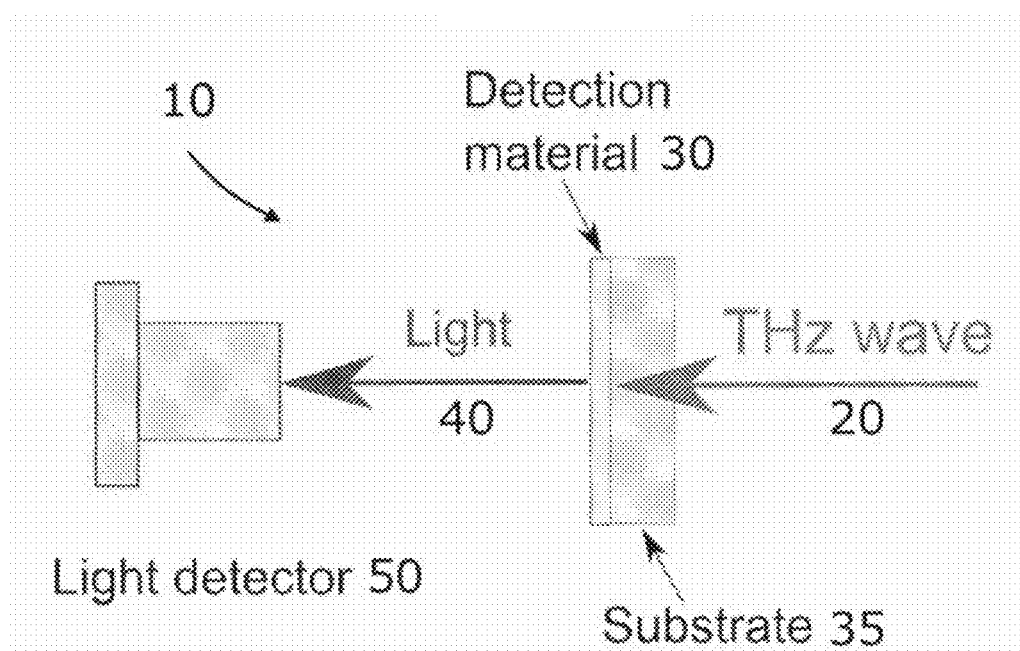
FIG. 1 schematically illustrates a system for THz wave detection through THz induced luminescence, FIG. 2 schematically illustrates a graph of the intensity of UV light generated in a metallic layer as a function of the peak electric field of the incident THz wave.

FIG. 1 schematic illustrates a system 10 for THz wave 20 detection through THz induced luminescence of structured metallic layers 30.

Here the system 10 for detecting terahertz radiation, indicated by the incident wave 20, comprises an input configured for receiving the terahertz radiation 20. For simplicity the input is not illustrated in FIG. 1 but may be a lens or other device focusing and/or directing the terahertz wave onto a metallic layer 30 arranged for receiving the terahertz radiation 20 from the input. The metallic layer 30 comprises an arrangement of metallic structures or apertures in a metallic film. An optical signal 40 is emitted from the metallic layer 30. Here the optical signal is illustrated by the arrow 40 but emission may be more distributed, e.g. more omnidirectional or spherically distributed than illustrated here.

The metallic layer 30 is free-standing or may be supported by a substrate 35. In FIG. 1 the substrate 35 is positioned at the side of the incident THz field, but the substrate may be positioned at the opposite side as well, either alone or in combination so as to have substrate at both sides. Positioning the substrate at the side opposite the incident THz wave requires an opening for the generated optical signal to pass through or that the substrate is transparent to this generated optical signal, alternatively a detector may be placed at the incident/reflection side.

Figure 3:
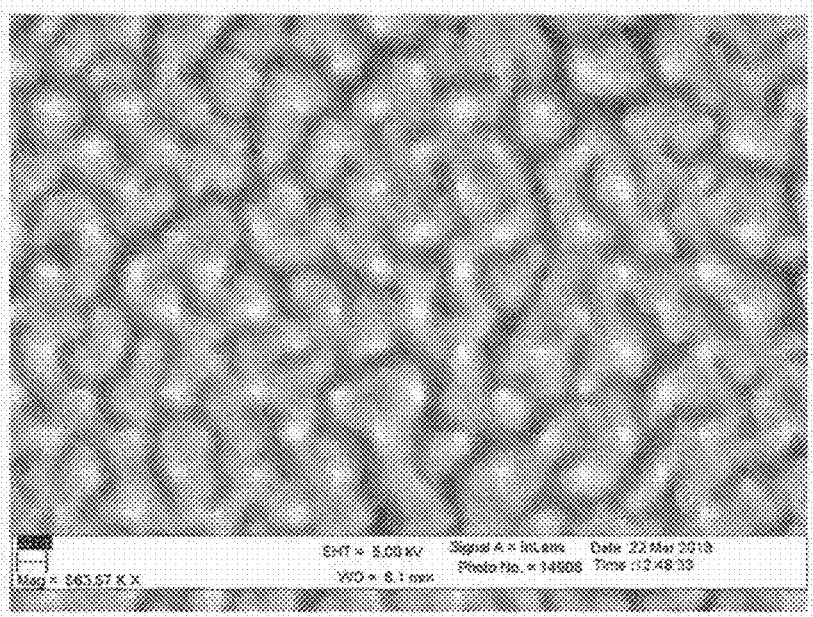
FIG. 3 is a SEM image of a metallic layer having a random structure obtained by gold deposition on high resistivity silicon wafer.
Figure 4:
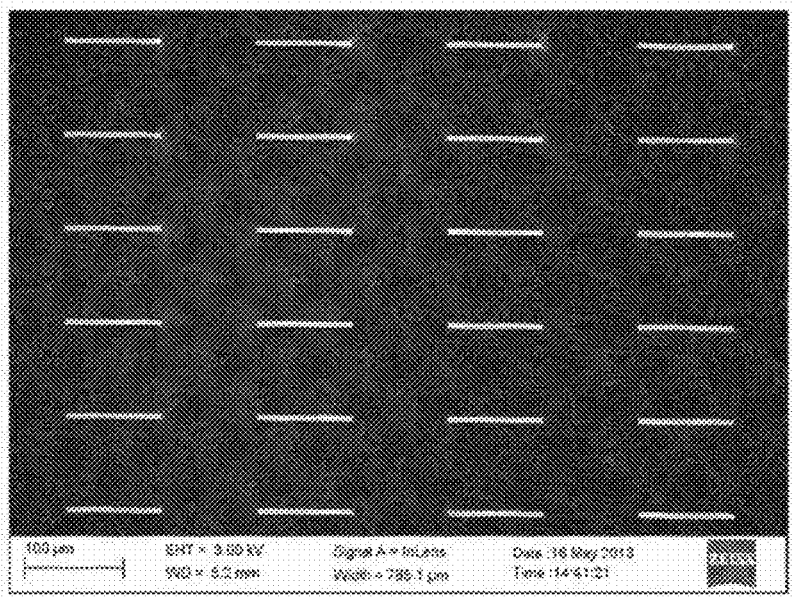
FIG. 4 is an SEM image of a structured metallic layer having a series of approximately 100 µm long, 4 µm wide and 0.2 µm thick gold bars manufactured by UV lithography on a high resistivity silicon wafer.

These metallic structures may be of the types as illustrated in FIGS. 3 and 4. In FIG. 3 the layer is formed by a process where metal is deposited on a surface, whereby more or less random structures are formed. The thickness of the metallic layer may be as small as 1 nm. In the process inevitably small areas will be formed where no metal is deposited thus forming openings or apertures. Generally any type of metal may be used for this layer, and experiments have shown that especially gold has advantageous luminescence properties in this setup. The terahertz radiation starts series of nonlinear physical processes involving conduction electrons of the metal that as a result lead to photon emission, illustrated as optical signal 40.

At least part of the emitted light or optical signal 40 is directed at an optical sensor 50 arranged to detect the emitted optical signal and to provide a signal indicating a property of the terahertz radiation. Reflectors and lenses may be incorporated into the system to enhance the focus and detection of the optical signal 40. The signal outputted from the detector or optical sensor 50 may be an electrical signal and may be fed to a signal processor for analysis of the electrical signal. On the basis of the signal from the optical detector 50 characteristics of the terahertz may be determined. The metallic layer 30 may be composed of several layers, e.g. with spacing layers of substrate in between or formed in direct contact. Having several metallic layers also allows for different metals to be used in the different layers.

By engineering resonant properties of the metallic layer 30 in the terahertz range, narrowband and broadband detection of terahertz radiation is possible. Random structures, like the one presented on FIG. 3, generally give broad frequency response, while resonant metamaterial structures, like the one presented on FIG. 4, provide narrowband response. Through intentional design of the metamaterial structure (its shape, length, width, thickness) the resonant properties (central frequency, the bandwidth and strength) of the THz detector can be changed. Also, by engineering field enhancement properties of the metallic layer 30 the sensitivity range of the terahertz detector can be changed.

Further, by engineering the symmetry properties of the metallic layer or layers 30, polarization sensitive as well as polarization insensitive detection can be easily achieved. In general random structures, like the one presented on FIG. 3, are polarization insensitive, while resonant metamaterial structures, like the one presented on FIG. 4, provide polarization sensitive response of the proposed THz detector. Through intentional design of the metamaterial structure, its symmetry, shape, length, width, thickness, detection of linearly, elliptically and circularly polarized THz waves can be achieved.

Because of the strong nonlinearity of the generated light as a function of the incoming terahertz field, the temporal response of the proposed method is significantly faster than the oscillation period of the detected THz wave.

For example: for a detector designed for terahertz radiation with frequency of 1 THz, the detection time is shorter than 1 picosecond. The main limitation of the detection time is thus the response time of the light detector 50.

Another advantage of the present invention is that the method is background free, meaning that no optical signal, i.e. no UV-VIS-NIR, is emitted in the absence of a terahertz field, and thus high sensitivities and high signal-to-noise ratio can be reached. In a method relying on thermal radiation, any background heat will cause a varying background noise signal to be detected.

Figure 2:
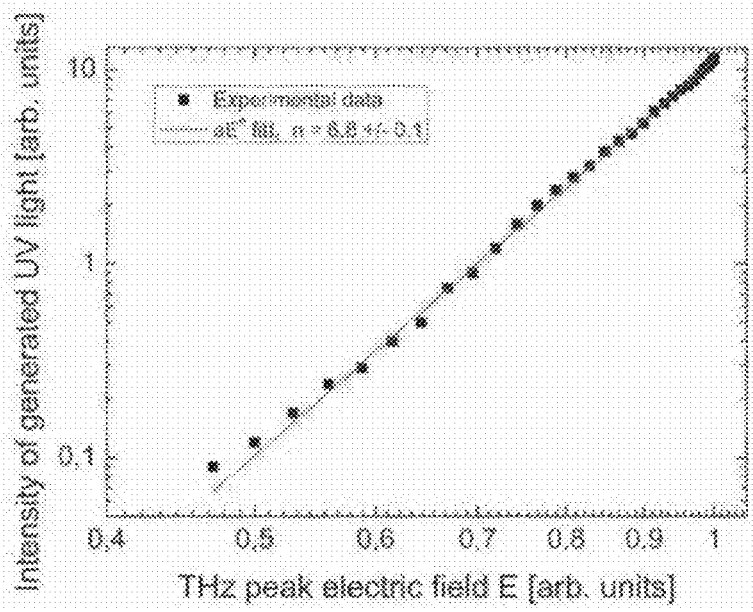

FIG. 2 is a graph illustrating the intensity of UV light generated in 7.6 nm-thick layer of percolated gold as function of the peak field of the incident THz wave. The intensity scales approximately with the $7^{th}$ power of the peak THz electric field.

FIG. 3 is a SEM image of a gold surface at the percolation threshold, with an average thickness of gold of 7.6 nm and gold coverage of 62% of the surface. As can be seen in the image, several areas exist where there is no metal. This results in inhomogeneity in the metal surface which in turn results in local areas with extreme enhancement of the incoming terahertz electric field. This field enhancement strongly magnifies the nonlinear processes at the surface, as described above, so that an optical signal may be emitted. This is referred to as terahertz induced luminescence.

FIG. 4 is an image of a surface where metal structures are intentionally designed and arranged into a metallic layer. Each of the structures is an approximately 100 μm long, 4 μm wide and 0.2 μm thick gold bar. The sample has been manufactured by UV lithography on a high-resistivity silicon wafer. Each of the structures forms a terahertz antenna, which emits UV-VIS-NIR light in a strongly nonlinear response to a terahertz signal being applied.

In both embodiments illustrated in FIG. 3 and FIG. 4 it is possible to engineer the resonant properties of the metallic layer or layers in the terahertz range so as to obtain desired narrowband and/or broadband detection of terahertz radiation. This could be done by varying shape, size, thickness, spacing between structures, type of metal used of manufacturing and properties of the substrate. Also, by engineering field enhancement properties of the metallic layer the sensitivity range of the Terahertz detector may be changed. The metallic layer can be seen as structured, either purposefully laid out as in FIG. 4 or randomly as in FIG. 3. The randomness of the structure in FIG. 3 may be at least partly controlled in the deposition and/or evaporation process, depending on the chosen manufacturing process.

Through experiments the inventors have shown that it is possible to detect terahertz radiation through terahertz induced luminescence. Also, they have shown that the spectrum of the generated light extends from UV, through VIS to NIR and that it depends on the properties of the metallic structured layer. The experiments carried out by the inventors prove that the physical mechanism underlying the invention is a three-step process which involves terahertz-induced field emission of electrons from the metal, acceleration of the electrons in the THz field, and collision of the electrons either with gas molecules in the atmosphere above the metal (nitrogen and oxygen) or collision between the electrons and the metal surface when the electrons return to the metal after the acceleration period. UV-VIS-NIR light is emitted as a result of subsequent deexcitation of the gas molecules or deexcitation of localized surface plasmons of the metal surface.

The inventors have also experimentally shown that the emitted spectrum is strongly affected by gas composition surrounding metallic layer. That effect can allow the proposed invention to be used as a gas sensor. Analysing the emitted spectrum then allows detection of which gas is present at the sensor. The data from the emitted spectrum may be analysed using a computer or other data analysis apparatus with information on different spectrum for different gasses.

Experimentally it has been verified that broadband detection, by observing UV-VIS-NIR light generated in layers of nanostructed thin gold films at the percolation transition is possible. Further narrowband detection, by observing UV-VIS-NIR light generated from resonant THz dipole antennas.

Figure 6:
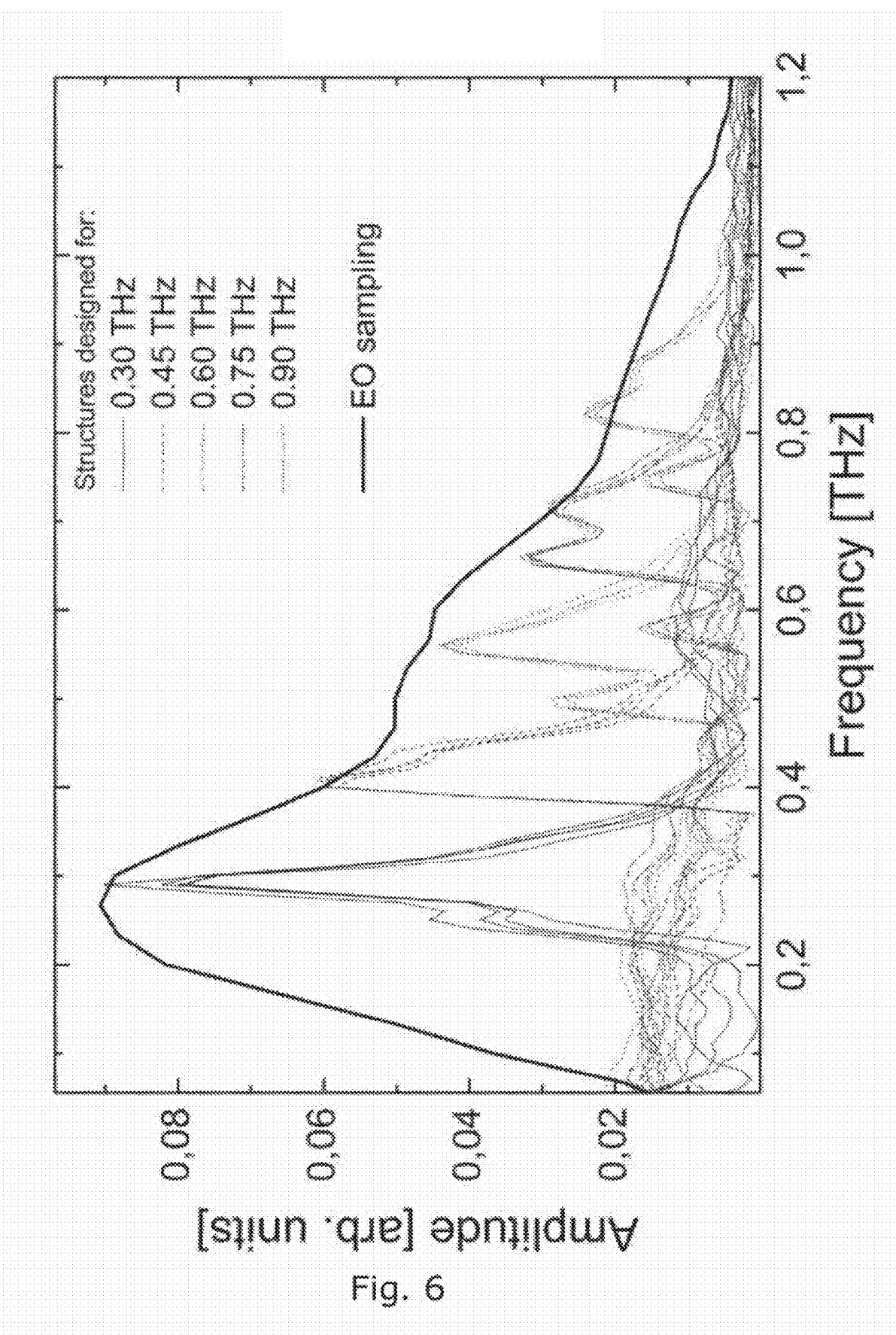
FIG. 6 is a schematic illustration of spectral response of various metallic structures.

The inventors have also shown that engineering, or changing, the resonant properties of THz dipole antennas it is possible to change the bandwidth of THz detection. This is illustrated in FIG. 6. FIG. 6 illustrates that a desired bandwidth may then be obtained by a properly designed resonant property. FIG. 6 illustrates the spectral response of various metallic structures designed for several THz frequencies compared with a spectrum of a THz pulse obtained using electro-optic sampling. The figure illustrates spectral response for metallic structures designed for 0.30, 0.45, 0.60, 0.75 and 0.90 THz.

Figure 7A:
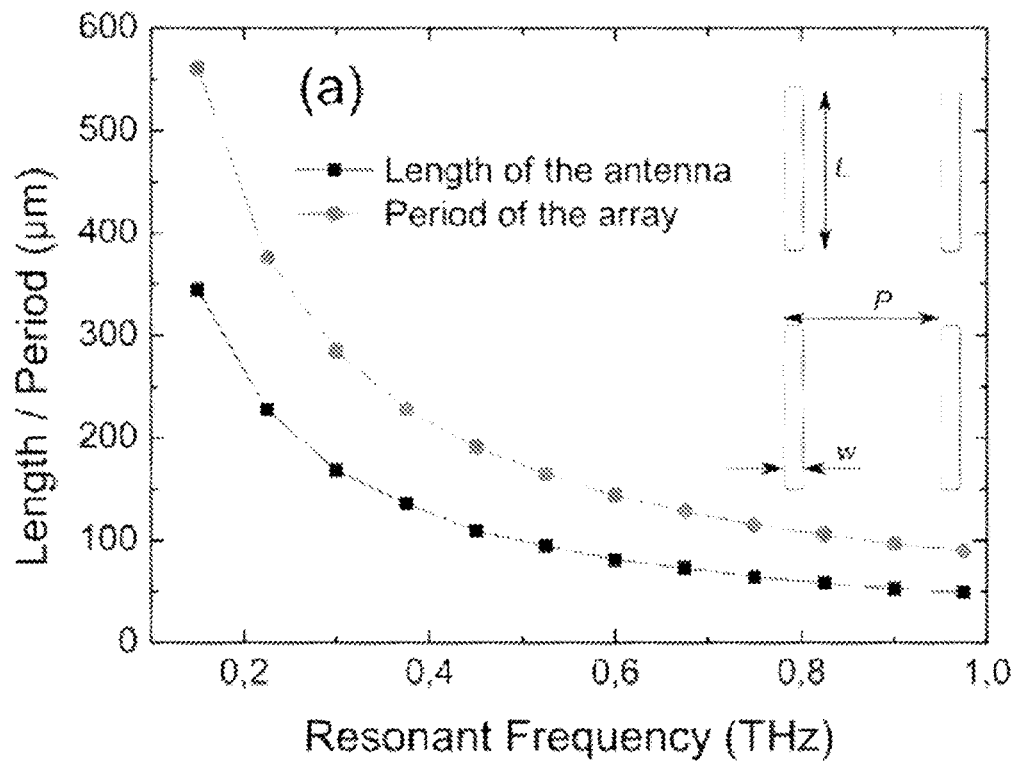
FIGS. 7a and 7b illustrate calculated dimensions of two different shapes.
Figure 7B:
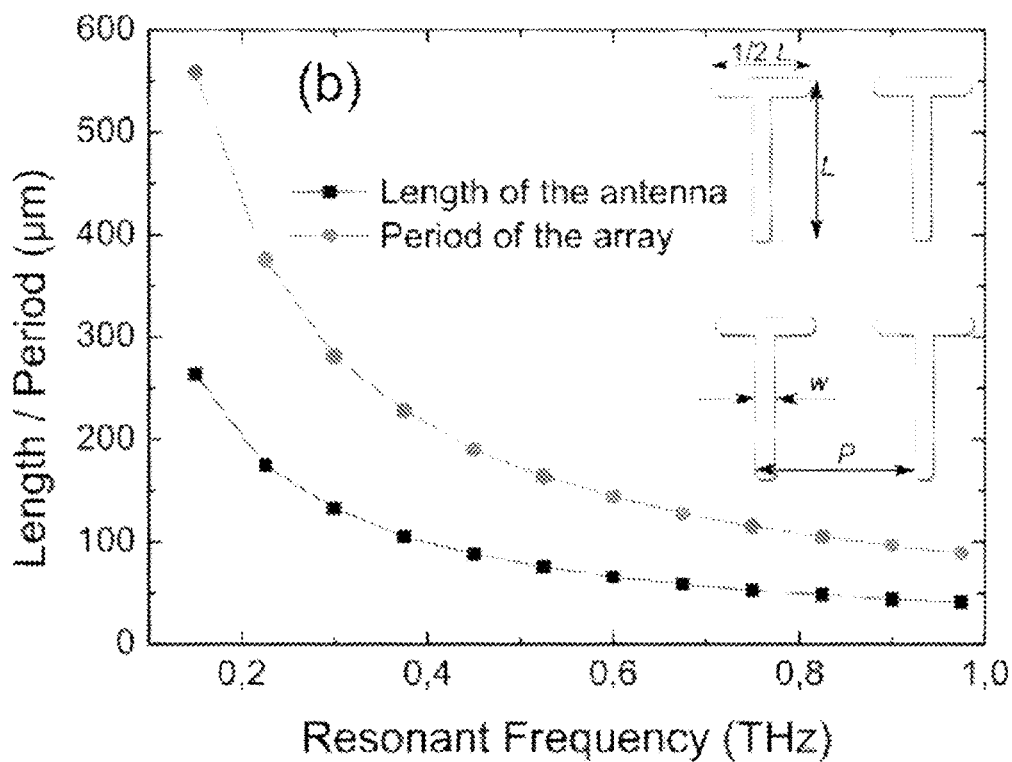

FIGS. 7a and 7b show further optimization of micro-antenna designs. FIG. 7a examines the case of a dipole antenna, or in other words an I-shaped antenna, and shows calculated length dimensions and spacings or periods for a given desired resonance frequency of the terahertz radiation, and optimized to yield the highest field enhancement. In the calculations, a gold antenna having a fixed width of 5 µm and a fixed thickness of 200 nm was assumed. The gold forming the antenna was considered to be deposited onto a high resistivity Silicon (HR-SI) substrate. The calculations shown in FIG. 7b are performed on a similar system as in FIG. 7a, except that a T-shaped antenna was studied. As illustrated, the length of the T top-bar was fixed in the calculations as half the length of the antenna. While these calculations show promising starting points for optimization of antenna layouts for a desired application, micro-antennas of other shapes, dimensions and/or metals may be advantageous for certain applications, e.g. for obtaining a desired bandwidth.

During the experiment the inventors demonstrated that the response time of the detector is faster than half of the oscillation period of the incoming THz wave. This is advantageous in obtaining an accurate and reliable detector.

Furthermore, in the embodiments illustrated and discussed it has been shown that the device does not require cooling. This enables less bulky and less expensive equipment. Also, not requiring cooling provides a more energy efficient apparatus.

Figure 5:
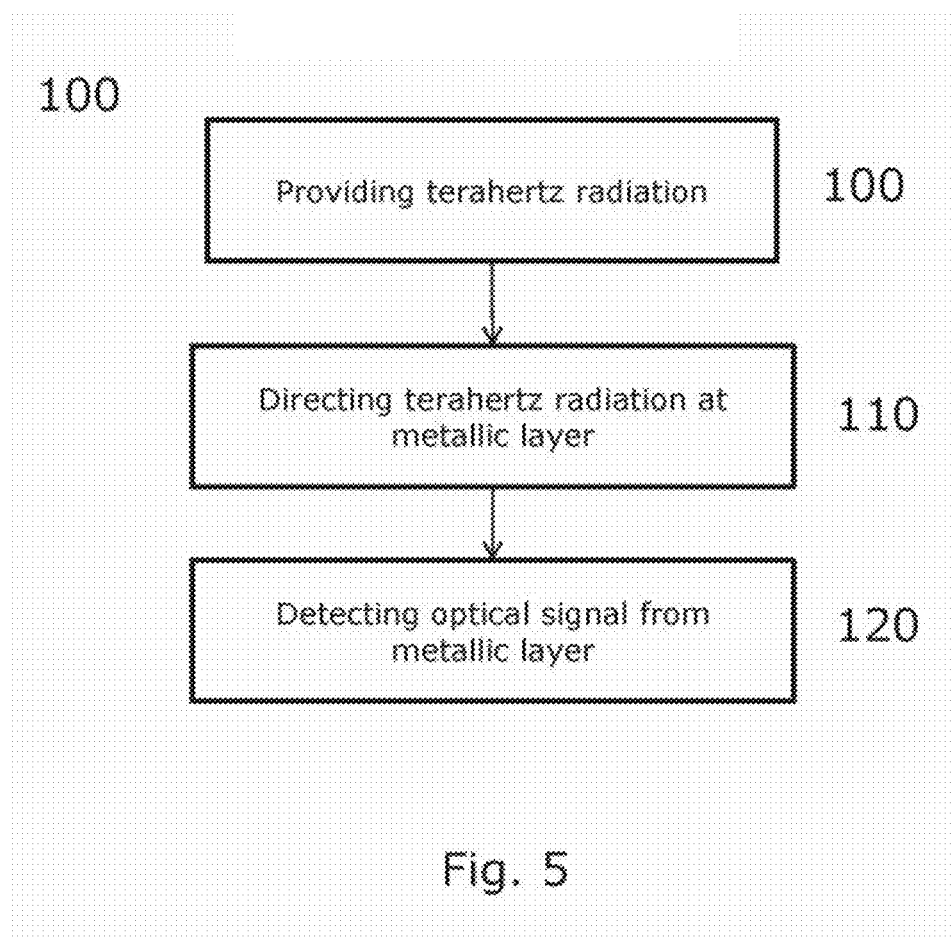
FIG. 5 is a schematic block diagram of steps of a method of detecting THz waves.

FIG. 5 is a schematic illustration of steps of a method for detecting terahertz radiation. The method comprises a step 100 of providing the terahertz radiation at an input. The method comprises a step 110 of directing the terahertz radiation at a metallic layer from the input, wherein metallic layer comprises an arrangement of metallic structures or apertures in the metallic film, the metallic layer emits an optical signal in response to the terahertz radiation. The method comprises a step of detecting the emitted optical signal at an optical sensor to provide a signal indicating a property of the terahertz radiation.

The method may be implemented as software and at least some of the steps executed on a digital processor or the like.

The invention can be implemented by means of hardware, software, firmware or any combination of these. The invention or some of the features thereof can also be implemented as software running on one or more data processors and/or digital signal processors.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A system for detecting terahertz radiation comprising:
   an input configured for receiving the terahertz radiation,
   a metallic layer configured for receiving the terahertz radiation from the input, wherein the metallic layer comprises an arrangement of metallic structures or apertures in a metallic film, wherein the metallic layer emits an optical signal in response to the terahertz radiation, and wherein the emitted optical signal is comprised of wavelengths shorter than those of which the terahertz radiation is comprised, and
   an optical sensor configured to detect the emitted optical signal and to provide a signal indicating a property of the terahertz radiation.

2. The system according to claim 1, wherein the metallic layer is arranged on a substrate.

3. The system according to claim 2, wherein the metallic layer is deposited on the substrate and the structure is randomly formed during a deposit process.

4. The system according to claim 1, wherein the metallic layer comprises a plurality of structures or apertures.

5. The system according to claim 4, wherein each of the structures comprises a rectangular geometry or a T-shaped geometry.

6. The system according to claim 1, wherein the detector outputs a signal, which is correlated to the peak field strength of the THz field.

7. A camera device comprising the system of claim 1.

8. The camera device according to claim 7, comprising a 2D array of detectors and optical sensors for establishing a set of signals representing a 2D image.

9. A method for analyzing a gas, comprising:
introducing a gas into the system of claim 1; and
performing a spectral analysis of ultraviolet, visible and near-infrared (UV-VIS-NIR) light on the gas after irradiation of the gas with a terahertz wave in the terahertz radiation detector.

10. A method for detecting terahertz radiation comprising:
providing terahertz radiation at an input,
directing the terahertz radiation at a metallic layer from the input, wherein the metallic layer comprises an arrangement of metallic structures or apertures in the metallic film, wherein the metallic layer emits an optical signal in response to the terahertz radiation, and wherein the emitted optical signal has a frequency falling within the one of the ultraviolet, visible, and near infrared ranges, and
detecting the emitted optical signal at an optical sensor to provide a signal indicating a property of the terahertz radiation.

11. The method according to claim 10, wherein the method is performed as a computer implemented method on a computer device.

\* \* \* \* \*